(12) United States Patent
Colaco Covas et al.

(10) Patent No.: US 7,380,442 B2
(45) Date of Patent: Jun. 3, 2008

(54) ON-LINE ROTATIONAL/OSCILLATORY RHEOMETRICAL DEVICE

(75) Inventors: Jose Antonio Colaco Covas, Braga (PT); Joao Manuel Luis Lopes Maia, Braga (PT); Pedro Antonio Moreira Machado Costa, V. N. Famalicao (PT)

(73) Assignee: Universidade Do Minho, Braga (PT)

( * ) Notice: Subject to any disclaimer, the term of this patent is extended or adjusted under 35 U.S.C. 154(b) by 0 days.

(21) Appl. No.: 11/058,422

(22) Filed: Feb. 16, 2005

(65) Prior Publication Data

US 2005/0235741 A1    Oct. 27, 2005

(30) Foreign Application Priority Data

Feb. 16, 2004    (PT)    ..................................... 103076

(51) Int. Cl.
*G01N 11/04*    (2006.01)
(52) U.S. Cl. .................... 73/54.28; 73/54.38; 73/54.39
(58) Field of Classification Search ............... 73/54.28, 73/54.38, 54.39
See application file for complete search history.

(56) References Cited

U.S. PATENT DOCUMENTS

| | | | | |
|---|---|---|---|---|
| 4,468,953 A | * | 9/1984 | Garritano | 73/54.39 |
| 4,539,838 A | * | 9/1985 | Fraleigh | 73/54.23 |
| 6,534,010 B2 | * | 3/2003 | Sentmanat | 422/68.1 |

FOREIGN PATENT DOCUMENTS

| | | | | |
|---|---|---|---|---|
| PT | 101941 A | * | 6/1998 | |
| PT | 102163 A | * | 12/1999 | ................ 73/54.04 |

OTHER PUBLICATIONS

Machado, A.V. et al. "Evolution of Morphology and of Chemical Conversion Along the Screw in a Corotating Twin-Screw Extruder," Journal of Applied Polymer Science, vol. 71, 1999, pp. 135-141.*
Carneiro, O.S. et al., "Experimental and Theoretical Study of Twin-Screw Extrusion of Polypropylene," Journal of Applied Polymer Science, vol. 78, 2000, pp. 1419-1430.*
Covas, J.A. et al., "Rheological Measurements Along an Extruder with an On-Line Capillary Rheometer," Polymer Testing, vol. 19, 2000, pp. 165-176.*
Covas, J.A. et al., "Online Monitoring Techniques for Studying Evolution of Physical, Rheological and Chemical Effects Along the Extruder," Plastics, Rubbers and Composites, vol. 33, No. 1, Jan. 2004, pp. 55-61.*

* cited by examiner

*Primary Examiner*—Daniel S. Larkin
(74) *Attorney, Agent, or Firm*—Sughrue Mion, PLLC

(57) ABSTRACT

The present invention refers to an on-line rotational/oscillatory rheometrical device inserted in the barrel of an extruder (1), composed of a main body (2), a cleaning ring (5) and a lower support (6), kept at a constant temperature, and a set of plates, upper (3) and lower (4) with an adjustable separation, with the upper plate being animated with a rotating or oscillating movement, via a coupling to a rotation/measuring head of a commercial controlled-stress rheometer. The rotation of the ensemble allows a sample of material to be collected from the interior of the extruder and its subsequent rheological characterisation in the device.

15 Claims, 5 Drawing Sheets

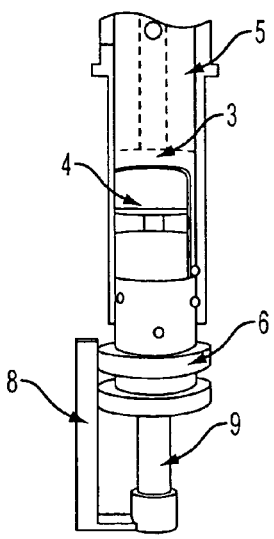
FIG. 3a
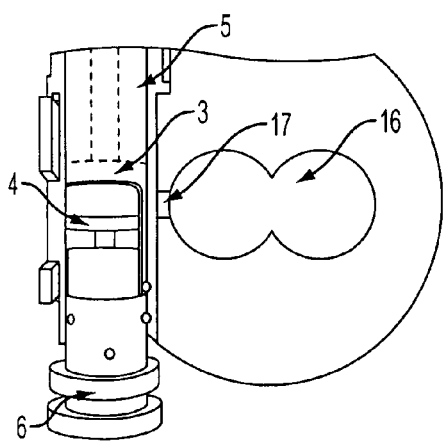 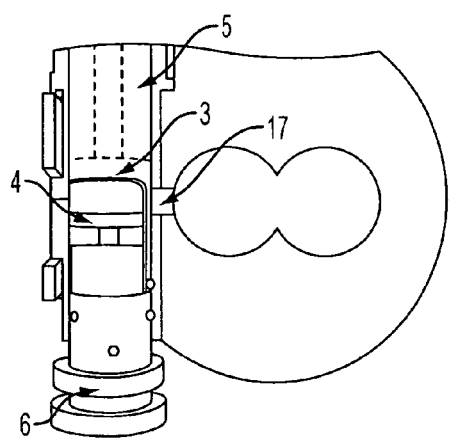
FIG. 3b     FIG. 3c
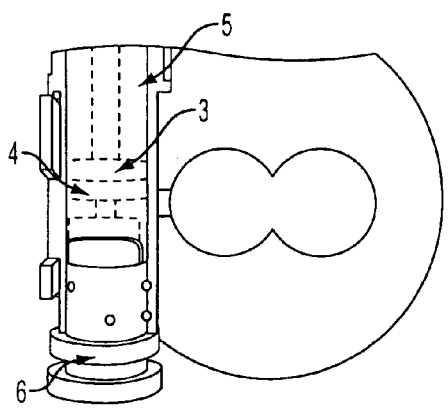 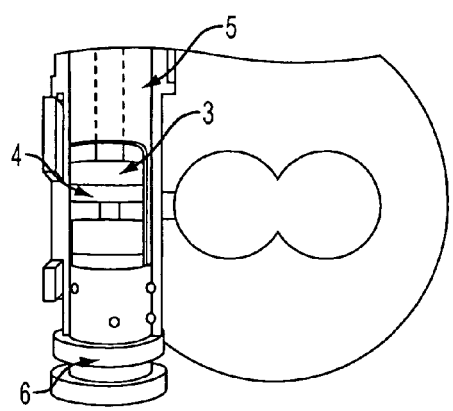
FIG. 3d     FIG. 3e

ON-LINE ROTATIONAL/OSCILLATORY RHEOMETRICAL DEVICE

CROSS-REFERENCE TO RELATED APPLICATIONS

This application claims priority from Portuguese Patent Application No. 103076 filed Feb. 16, 2005.

THEME OF INVENTION

The objective of on-line rheometry is the rheometrical characterisation of materials during their processing in an industrial environment. The data thus obtained can be used in the monitoring of the process with a view to automatic process or quality control [1]. With respect to polymer compounding and reactive extrusion in particular, it is crucial that the generated data be sensitive to the morphological evolution (average size of the dispersed phase in immiscible polymer blends, for example), to the thermal-mechanical history (important, for example, in determining the average fibre length in composites) and to the chemical evolution (for example, in in-situ compatibilisation of reactive systems) that occur along the extruder.

STATE-OF-THE-ART

The on-line systems developed thus far resort to capillary or slit rheometers that, once inserted between the extruder and the die, are fed by a secondary flow bypassed from the extruder and by a gear pump, which determines the flow rate into the metering zone [2, 3]. One of the rare exceptions is the geometry based on the "partial Couette", proposed by Dealy, that could be integrated in the die [4]. The main limitations of this type of rheometer are: i) the time-lag in the measurements, that are only possible after the melt flows to the capillary/slit, to which the residence time inside the extruder must be added, ii) the test is a destructive one, i.e., it changes the initial morphology and iii) the instrument is located between the extruder and the die where, under normal conditions, the morphology or chemical reaction will have already achieved steady-state or have been completed. As a consequence, the available instruments have revealed to be useful for the quality control of processes, but not for tracking the evolution of properties/characteristics along the extruder.

Recently, a system was developed that adapted a capillary rheometry geometry [5] to sample-collecting valves [6], which allows the first and third of the above shortcomings to be overcome, since the material to be characterised is quickly removed and placed in the measuring system, which, in turn, is placed at any location along the extruder.

The present invention refers to equipment that can be coupled to a rotational rheometer and allows the non-destructive measurement of rheological properties during extrusion, thus overcoming the second shortcoming above. This equipment is based on the working principle of rotational rheometers in which the material is located between two plates, in the case of a parallel-plate geometry, or between a plate and a shallow angle cone (less than 6°, so that cos β, where β is the cone angle, is approximately equal to unity), in the case of the cone-and-plate geometry.

The latter geometry has the advantage of imparting a constant shear rate to the whole sample and allowing stress relaxation experiments to be performed in a straightforward fashion. Considering steady state, laminar and isothermal flow, neglecting the effect of gravity and inertia, the shear stress is then approximately constant throughout the fluid and is given by [7]

$$\sigma = \frac{3M}{2\pi R^3} \quad (1)$$

where R is the plate radius and M is the measured torque. The shear rate is then approximately equal to (the errors being typically smaller than 2%):

$$\dot{\gamma} = \frac{\omega}{\beta} \quad (2)$$

where ω is the angular frequency. The viscosity is given by the ratio between the shear stress and the shear rate and, thus, implies the measurement of the torque at different rotation speeds in order for a flow curve to be obtained.

The parallel-plate geometry is a popular alternative to the former in the study of rubbers, molten polymers and highly viscous materials in general, due to the simple sample loading procedure. However, the deformation is not homogeneous as the fluid is submitted to a range of shear rates varying from zero at the center to a maximum at the rim. Assuming the same simplifications as previously, the shear stress is now given by $$\sigma = \frac{M}{2\pi R^3}\left[3 + \frac{d\ln M}{d\ln \dot{\gamma}_r}\right] \quad (3)$$

Equation (3) implies that in order to determine the shear stress of an unknown fluid, sufficient ln M data as a function of ln $\dot{\gamma}_R$ (the shear rate at the rim) has to be generated in order for the derivative to be calculated accurately.

Rotational rheometers that resort to these two geometries allow, in general, an oscillatory strain, usually of a sinusoidal nature, to be induced under controlled conditions, in addition to the steady-state experiments above. This type of dynamical analysis is frequently adopted in the study of the linear viscoelastic behaviour of fluids since in the region of small strains the material functions are independent of the amplitude of the deformation. This implies that these tests are of a non-destructive nature. Thus, quantities like the complex modulus G*, and its components, the storage modulus G', representing the elastic part of the response) and the loss modulus G", representing the viscous part of the response, as well as the complex and dynamic viscosities, η* and η', may be measured [8].

The response to these deformations characterizes physical interactions, e.g., entanglements, and chemical interactions, e.g., crosslinks, only if the maximum amplitude is kept small enough. The limits of linear viscoelastic behaviour may range from less than 1% strain for some weakly structured systems, such as foodstuff, and more than 1000% for some gels. For example, typical maximum strain ranges from 0.05 for soups and low-viscosity emulsions, to 0.1 for paints and chocolates, 0.4 for polymers, 1.0 for margarines and dispersions and 50 to 100 to biopolymer gels and solutions. The commercial instruments currently in use allow experiments to be performed up to angular frequencies in excess of 300 rad/s.

The present invention allows a commercial rheometer head, with the above typical characteristics, to induce the strain and measure the corresponding torque or vice-versa, of samples removed locally from the extruder along its length, in either a parallel-plate or a cone-and-plate geometry. In addition, it is possible to use the software of the instrument, which is capable of calculating automatically the variation of the rheological response as a function of shear strain/stress in order to measure other material functions, such as the ones in small amplitude oscillatory shear.

REFERENCES

[1] J. M. Dealy and K. F. Wissbrun, *Melt rheology and its role in plastics processing*, Van Nostrand Reinhold, New York, 1990
[2] Goettfert Werkstoff-Prufinaschinen GmbH, Real Time Rheometer RTR-RTS, Patents BP 3921 841.4-.09, BP 42 36 407, EP 04 06 805, U.S. Pat. No. 5,172,585
[3] Goettfert Werkstoff-Prufinaschinen GmbH, Mini Byass Rheograph MBR.
[4] J. M. Dealy, U.S. Pat. No. 4,571,989.
[5] Patente portuguesa 102163, 2000
[6] Patente portuguesa 101941, 1999
[7] J. A. Covas e J. M. Maia, *Reometria*. In A. G. Castro et al (eds.)—*Reologia e Suas Aplicações Industriais*. Colecção "Ciência e Técnica", Instituto Piaget, Lisboa, 2001. pp. 89-130.
[8] C. W. Macosko, *Rheology Principles, Measurements and Applications*, VCH Publishers, NY, (1994)

SUMMARY OF THE INVENTION

The on-line rotational/oscillatory accessory that is the object of the present invention aims to keep the general working principles and functionalities of commercial rotational/oscillatory rheometers, whilst coupling it to the cylinder of an extruder. The equipment is installed vertically via insertion in an orifice drilled in a cylinder segment. This has a second horizontally drilled orifice that communicates with the interior of the extruder. The invention is constituted by a hollow rotating cylinder, inside which are two parallel plates, or a cone-and-plate, with upper element rotating/oscillating during an experiment, via the coupling with the head of a commercial rheometer. The lower element is connected with a position transducer placed on its base.

The equipment has three main functions activated sequentially: (see FIG. 3c) to collect a quantity, usually a few grams, of material from inside the operating extruder for characterisation, d) to prepare a sample with an adequate geometry for the experiment and e) perform the measurement.

In order to perform the first function, the equipment resorts to the concept of a sample-collecting device, corresponding to Portuguese patent 101941 of 1999. The geometry of the sample is obtained by the compression of the material collected in the chamber formed by the upper and lower surfaces, the distance between them being adjustable, and an outer ring that slides in order for the cylinder-shaped sample has a free lateral surface during measurement. The latter is performed by attaching the upper surface to the measuring/rotating head of a commercial controlled-stress rheometer, which has the necessary motor, sensors and control software.

The measurements consist in the rotation or oscillation of the upper plate for varying speeds/frequencies, usually at constant temperature, with the corresponding torque being measured.

BRIEF DESCRIPTION OF THE DRAWINGS

The on-line rotational/oscillatory accessory and respective components are illustrated in FIGS. 1 to 4.

FIG. 2 represents the equipment and all its components in detail. Thus.

FIG. 3 illustrates the working sequence in the phase of gap definition (3a), beginning of cycle (3b), sample collection (3c), waste removal (3d) and performance of the experiment (3e).

Figure 4:
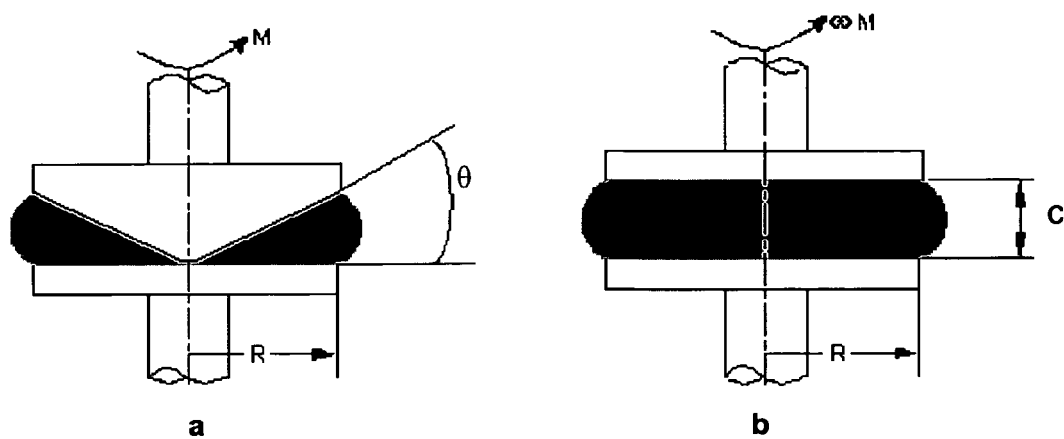

Finally, FIG. 4 details the geometry in both cone-and-plate (4a) and parallel-plate (4b) configurations.

DETAILED DESCRIPTION OF THE EXEMPLARY EMBODIMENTS OF THE INVENTION

To the best of the author's knowledge, there are no previous inventions with the same aim. There are a large number of commercial laboratory rotational rheometers where the sample is loaded manually. Likewise, there are various on-line rheometers (see, for example, patents BP 3921 841.4-.09, BP 42 36 407, EP 04 06 805, U.S. Pat. No. 5,172,585), that are designed to be inserted between the extruder and the die.

In Portuguese patent no. 102163, the concept of on-line capillary rheometry is used coupled to extrusion, with a capillary rheometer inserted in different locations along the extruder. In the present invention, the concept of real time rheological characterisation is recovered, but a different measuring technique is used—rotational/oscillatory rheometry—that provides information on the viscoelastic behaviour of the sample in a non-destructive way (in the case of small-amplitude oscillatory rheometry), unlike capillary rheometry that only measures the viscous properties in a destructive way. This latter capability is fundamental for the analysis of some systems, such as polymer blends, composites and foodstuff.

Figure 1:
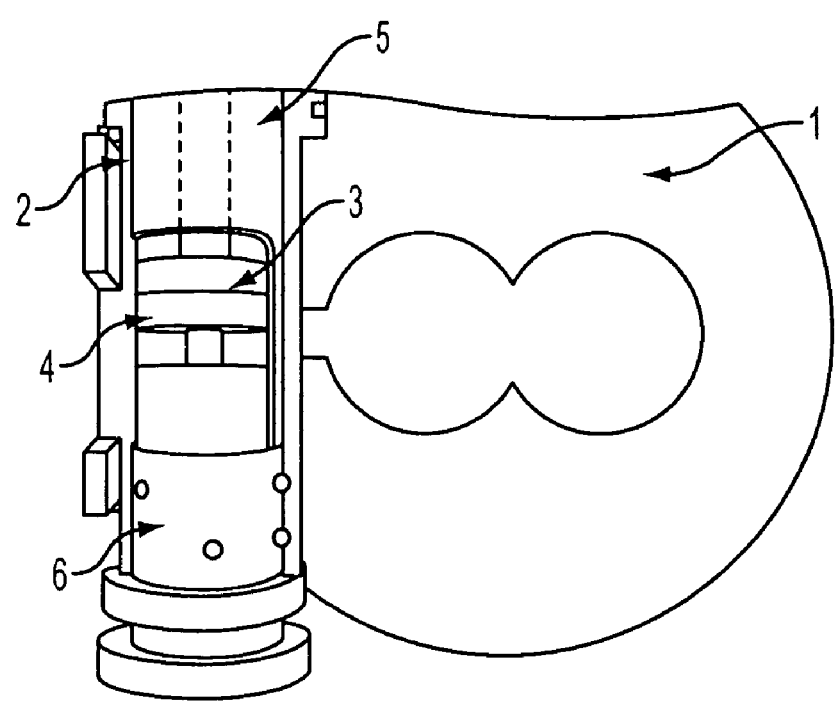
FIG. 1 shows the equipment mounted in twin-screw extruder, highlighting the main components, namely the main body, the upper and lower plates and the cleaning ring.
Figure 2A:
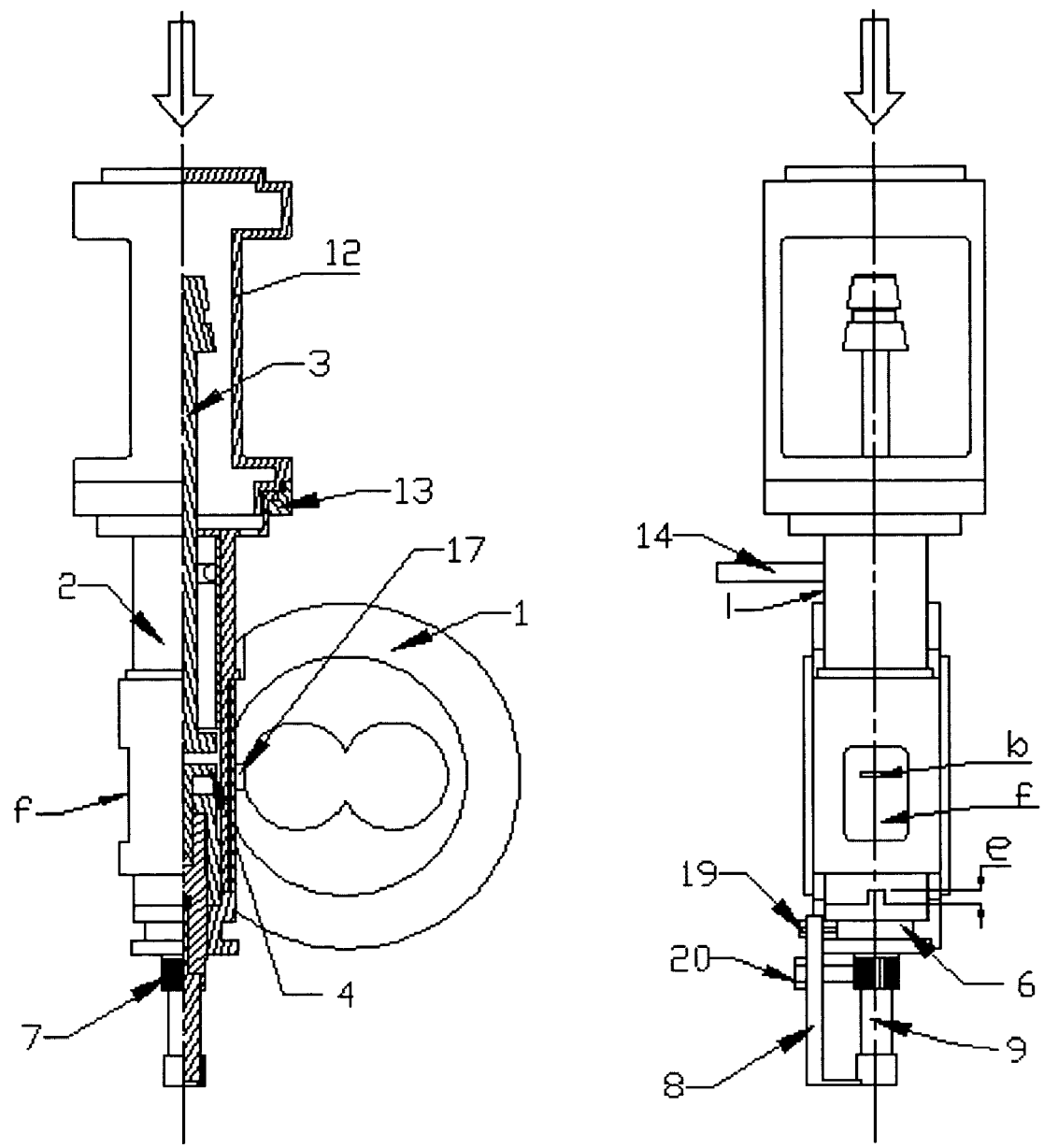
FIG. 2a shows the general construction of the instrument and its coupling to a conventional rotational/oscillatory rheometer.

The on-line rotational/oscillatory equipment (FIG. 2a), that constitutes the present invention, is constituted by a main body (2), that is inserted vertically in an insert of the extruder cylinder (1), which is an integral part of this invention. This insert is mounted between two adjacent extruder cylinder segments and, thus, its geometry will vary with the model and manufacturer of the extruder. The insert also contains an horizontally drilled orifice (17) that allows flow of the material from the extruder to the rheometer to take place.

Figure 2B:
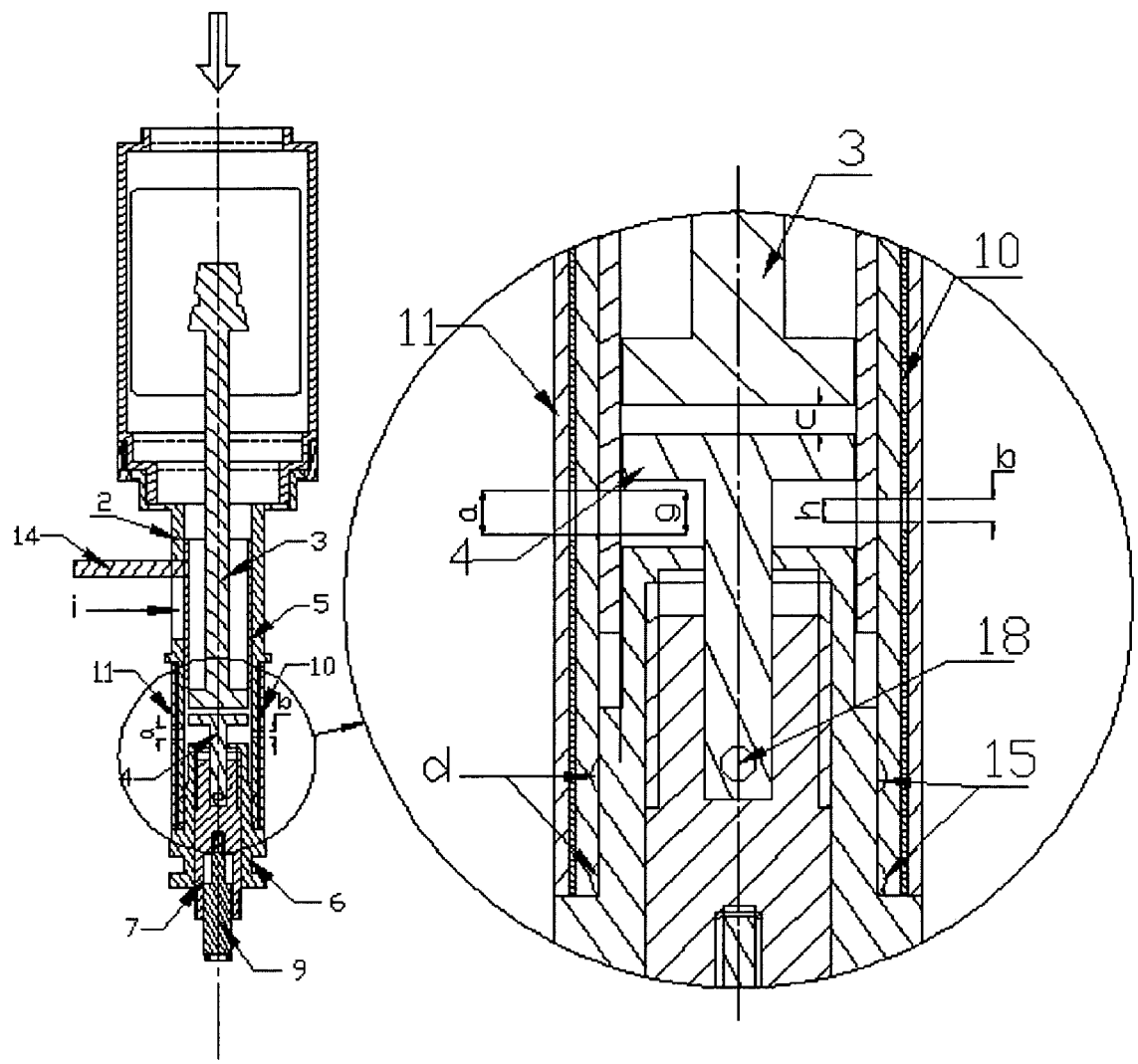
FIG. 2b complements the visualisation of the equipment and includes a partial blow-up of the metering zone.

The upper part of the main body of the rheometer (2) has larger dimensions than the remainder, so that, once inserted in the cylinder segment (1), the whole instrument is vertically immobilized. In turn, the lower part (6) is immobilized inside the main body (2), by means of two rows of spherical stoppers (15). The main body (2) also contains a set of orifices along its lateral wall that are used to set in motion the cleaning ring (5) through the stopper (14), allow the intake of material from the extruder (a, in FIG. 2b) and allow the elimination of the excess material (b, in FIG. 2b). The external surface of the lower part of the main body (2) is coated by a resistance (10) that, in turn is protected by a sleeve (11). The cleaning ring (5) has two orifices, (g) and (h), that align with the orifices (a) and (b) when the system is immobilized in the lower position.

The spherical stoppers (15) of the lower support (6) allow the vertical immobilization of the latter inside the main body (2) in two different positions, defined by the entrances (d, in FIG. 2b) of the lower wall of the body (2). In turn, the possible rotation of the support (6) in the main body (2) in the upper position is prevented by the existence of rectangular saliencies (e, in FIG. 2a). The support (6) is essentially made up of an external sleeve, inside which there is an adjustable screw (7). The lower plate is fixed to this screw through a stopper (18). One of the extremities of a LVDT (Linear variable Differential Transformer) strain transducer (9) is screwed to the inside of the screw (7). The other extremity of the LVDT transducer (9) is fixed to the part (8) that, in turn, is connected to the support (6) by means of a screw (19). This part (8) contains a screw (20) that is used to immobilize the screw (7).

The cone/plate (3) and the cleaning ring (5) are inserted inside the body (2) and above the support (6). The body of the measuring/rotating head of the commercial rheometer is coupled to the invention through an adapter (12) and a threaded ring (13). The sensor/actuator of the rheometer is coupled directly to the mast of the cone/plate (3) through its own tightening system.

In one embodiment the hollow main body (2) has a section with an external diameter of 54 mm and a main section with an external diameter between 30 and 33 mm and an internal one between 24 and 28 mm, which is partially coated with a resistance (10) with between 65 and 75 mm in length, protected by a sleeve (11). It has two opposite orifices (a) and (b), the thread (i) and the internal cavities (d) placed in two horizontal parallel rows.

In another embodiment the lower support (6) is located in the interior of the main body (2) and immobilized in the latter through parallel rows of spherical stoppers (15), distanced 8 to 12 mm apart, and by the rectangular saliencies (e) with 3 to 5 mm in height and 3 to 5 mm in width.

In another embodiment, the measuring system of the plate/cone type has a radius (R) of 5 mm and, in the case of the cone, an aperture angle between 1° and 6°.

In another embodiment, the measuring system of the parallel-plate type has a plate radius (R) of 5 mm.

FIG. 3 illustrates the main steps during an operating sequence of the present invention. FIG. 3a shows that before the body of the rheometer (2) is inserted in the extruder cylinder (1), one must set the desired gap (c) between plates (3) and (4) that will be used during the experiment. In order to do so, the support (6) is placed in the upper position and the screw is tightened until the two plates (3) and (4) touch each other. Then, screw (7) is unscrewed slowly until the sensor (9) indicates the intended gap and is immobilized by screw (20).

In FIG. 3b the equipment is ready to start an experiment. The lower support (6) is immobilized by the spherical stoppers (15) in the lowermost position and the orifice (a) of the main body (2) is out of sync with the inlet channel (17), in order to prevent the intake of material. Additionally, the cleaning ring (5) is immobilized in the lower position. By turning the main body (2) (see FIG. 3c), the inlet channel (17) is aligned with the intake orifice (a) and the pressurised material flows from the extruder (16) to the free volume inside the on-line rheometer until the excess material flows out from the outlet orifice (b) that is directly connected with the exterior through the opening (f) of the cylinder segment. The main body (2) is then rotated again in order to isolate the material inside from the inlet channel (17).

FIG. 3d shows the sample preparation stage. The cleaning ring (5) is moved up and the support (6) is placed in the upper position, i.e., the upper plate/cone and the lower plate are moved to the gap (c) previously defined. The cleaning ring (5) is then moved successively up and down in order to remove the excess material in the free surface of the sample which will then accumulate below the bottom plate. The material is left to equilibrate thermally in the experiment position.

A measurement/run can then be performed (FIG. 3e) by imposing a rotation/oscillation of the upper plate/cone at different shear rates/stresses and measuring the corresponding shear stress rates.

Once the experiment is finished, the whole rheometer head/part (12)/plate (3) set is removed from the top and the lower plate (4)/support (6)/LVDT (9) from the bottom. The main body remains in place in order to avoid the escape of material from the extruder by the inlet channel (17).

The invention claimed is:

1. A device for on-line rotational/oscillatory rheometry, comprising:
    a hollow main body having a first orifice on a side portion communicating an inside of the hollow body with an outside of the hollow body;
    a first surface rotatably disposed in a first portion of the hollow main body;
    a support disposed in a second portion adjacent to the first portion of the hollow main body;
    a gap setting member movably disposed inside at least a portion of said support;
    a second surface disposed in the second portion of the hollow main body between said support and said first surface and supported by the gap setting member;
    a position sensor connected to the support and the gap setting member,
    wherein the first surface is adapted to be connected to a rheometer for rotation or oscillation.

2. The device for on-line rotational/oscillatory rheometry according to claim 1, further comprising:
    an insert member disposed adjacent to an extruder and adapted to communicate with material within the extruder,
    wherein the hollow main body is mounted in the insert member that is connected to an inlet channel coming from the extruder.

3. The device for on-line rotational/oscillatory rheometry according to claim 2, wherein the insert member is in contact with a side of the extruder and communicates with the material through a horizontal orifice between the material and the insert.

4. The device for on-line rotational/oscillatory rheometry according to claim 1, wherein the hollow main body has a top section with an external diameter of 54 mm and a main section with an external surface having a diameter between 30 and 33 mm and an internal surface having a diameter between 24 and 28 mm, the internal surface is partially coated with a resistance and the main section has a length between 65 and 75 mm,
    wherein the external surface is protected by a sleeve having an orifice corresponding to the orifice of the hollow main body.

5. The device for on-line rotational/oscillatory rheometry according to claim 1, wherein the support is immobilized in the hollow main body by parallel rows of spherical stoppers distanced 8 to 12 mm apart, and by rectangular saliencies 3 to 5 mm in height and 3 to 5 mm in width.

6. The device for on-line rotational/oscillatory rheometry according to claim 1, wherein the support has a threaded interior in which the gap setting member is threaded.

7. The device for on-line rotational/oscillatory rheometry according to claim 1, wherein the gap setting member is between 50 and 60 mm in length and has a threaded diameter between 12 and 16 mm.

8. The device for on-line rotational/oscillatory rheometry according to claim 1, wherein the position sensor comprises a LVDT (Linear Variable Differential Transformers) sensor that is fixed to the gap setting member by means of a thread and fixed to the support by means of screw.

9. The device for on-line rotational/oscillatory rheometry according to claim 1, further comprising:
a stopper member that engages the gap setting member to immobilize the gap setting member.

10. The device for on-line rotational/oscillatory rheometry according to claim 1, further comprising: a mast connected to the first surface which couples the first surface to a sensor/actuator of a rheometer.

11. The device for on-line rotational/oscillatory rheometry according to claim 10, further comprising: an adaptor which connects the hollow main body to the rheometer.

12. The device for on-line rotational/oscillatory rheometry according to claim 1, wherein the first surface comprises a cone shape having a radius (R) of 5 mm and an aperture angle between 1° and 6°.

13. The device for on-line rotational/oscillatory rheometry according to claim 1, wherein the first surface comprises a substantially circular plate having a plate radius (R) of 5 mm.

14. The device for on-line rotational/oscillatory rheometry according to claim 1, further comprising:
a cleaning sleeve lining a portion of the inside of the hollow main body and movably positioned in the hollow main body to move between an upper position and a lower position, wherein in the lower position the cleaning sleeve surrounds an outer diameter of the first surface and the second surface, wherein the cleaning sleeve includes a first sleeve orifice which aligns with the first orifice of the hollow main body when in the lower position, and wherein when the cleaning sleeve is in the upper position a gap is formed surrounding the outer perimeter of the first surface and the second surface.

15. A system for measuring the rheometry of a material, comprising:

an extruder which extrudes the material;

an insert member disposed adjacent to the extruder and adapted to communicate with the material within the extruder;

a hollow main body having an orifice on a side portion communicating an inside of the hollow body with an outside of the hollow body and disposed in the insert member;

a first surface rotatably disposed in a first portion of the hollow main body and confronting a second surface disposed at a distance from the first surface;

a support disposed adjacent to the second surface opposite the first surface;

a gap setting member movably disposed inside at least a portion of said support to support said first surface; and a position sensor connected to the support and the gap setting member, wherein the first surface is adapted to be connected to a rheometer for rotation or oscillation and the orifice communicates with the material of the extruder via the insert member.

* * * * *